United States Patent [19]
Weisenberger et al.

[11] Patent Number: 5,677,466
[45] Date of Patent: Oct. 14, 1997

[54] LABELLED FIBRINOGEN RECEPTOR ANTAGONISTS, THE USE THEREOF AND PROCESSES FOR PREPARING THEM

[75] Inventors: Johannes Weisenberger; Hans-Dieter Schubert, both of Biberach; Günter Linz, Mittelbiberach; Karl-Heinz Switek, Biberach; Frank Himmelsbach, Mittelbiberach, all of Germany

[73] Assignee: Dr. Karl Thomae, GmbH, Biberach an der Riss, Germany

[21] Appl. No.: 477,667

[22] Filed: May 23, 1995

Related U.S. Application Data

[63] Continuation of Ser. No. 55,176, Apr. 28, 1993, abandoned.

[30] Foreign Application Priority Data

Apr. 28, 1992 [DE] Germany .......................... 42 13 930.9
Apr. 30, 1992 [DE] Germany .......................... 42 14 245.8

[51] Int. Cl.$^6$ ...................... C07D 207/26; C07D 207/263
[52] U.S. Cl. .......................... 548/518; 548/566; 548/136; 548/309.7; 548/336.1; 424/1.81; 544/59; 544/410; 544/242; 546/184
[58] Field of Search ...................... 548/250, 518, 548/566

[56] References Cited

U.S. PATENT DOCUMENTS

| 5,455,348 | 10/1995 | Austel et al. | 544/238 |
| 5,463,071 | 10/1995 | Himmelsbach et al. | 548/251 |
| 5,478,942 | 12/1995 | Himmelsbach et al. | 548/263.2 |

FOREIGN PATENT DOCUMENTS

| 0372486 | 12/1989 | European Pat. Off. . |
| 0381033 | 1/1990 | European Pat. Off. . |
| 0503548 | 3/1992 | European Pat. Off. . |
| 0483667 | 5/1992 | European Pat. Off. . |
| 0496378 | 7/1992 | European Pat. Off. . |
| 0525629 | 7/1992 | European Pat. Off. . |
| 0528369 | 2/1993 | European Pat. Off. . |
| 0381033 | 8/1993 | European Pat. Off. . |
| 4129603 | 9/1991 | Germany . |
| 4134467 | 10/1991 | Germany . |

OTHER PUBLICATIONS

"Low Molecular Weight, non–Peptide Fibrinogen Receptor Antagonists" J. Med. Chem. May 4, 1992, 35, 4393–4407.

*Primary Examiner*—Matthew V. Grumbling
*Attorney, Agent, or Firm*—R. P. Raymond; A. R. Stempel; M-E. M. Devlin

[57] ABSTRACT

The invention relates to new labelled fibrinogen receptor antagonists which have an affinity for the receptor which is comparable to or greater than that of $^{125}$I-fibrinogen and whose binding is not disrupted by foreign proteins.

10 Claims, 1 Drawing Sheet

Fig. 1

LABELLED FIBRINOGEN RECEPTOR ANTAGONISTS, THE USE THEREOF AND PROCESSES FOR PREPARING THEM

This is a continuation of application Ser. No. 08/055,176, filed Apr. 28, 1993 now abandoned.

In the normal course of events, i.e. when blood vessels are intact, the fluidity of the blood is maintained by the fact that none of the crucial haemostatic mechanisms is activated. In order to staunch the flow of blood in the case of injury, the following two processes are initiated:

1. The aggregation of thrombocytes which starts within seconds at the direct site of the vascular lesion, in order to initiate the staunching of the bloodflow by the clot which forms, and
2. the coagulation which occurs somewhat later and stabilises the clot by the formation of threads of fibrin.

This aggregation and coagulation can also occur on vascular walls which are not injured but have been changed by atherosclerotic plaques and thus give rise to life threatening diseases such as myocardial infarction, pulmonary embolism and stroke.

One preventive measure which would appear logical in such cases would be to prevent the initial formation of the clot. Various drugs which inhibit individual methods of thrombocyte aggregation have hitherto been used without any resounding success. The end stage common to all the inducers of activation is the formation of the clot which, the latest findings would suggest, is produced by thrombocytes being held together via the fibrinogen receptors present on the thrombocyte membrane, by means of the bifunctional, thread-like fibrinogen. If it were possible to prevent this process, the formation of the clot could be inhibited, irrespective of the method of activation (see Cahill, M. et al., Brit. J. Clin. Pharmacol. 33:3–9 (1992)).

In the search for fibrinogen receptor antagonists which block the fibrinogen receptor and thus inhibit the binding of fibrinogen to the thrombocytes, a method is needed to allow quantitative measurement of this binding. A standard method is the use of $^{125}$I-fibrinogen and the separation of cell-bound and free fibrinogen by centrifuging. This process has the following serious drawbacks:

1. The nuclide used is a γ-emitter
2. The half-life is only 60 days
3. Fibrinogen is an adhesive protein
4. The binding is not totally reversible
5. The method cannot be used in the presence of plasma
6. The thrombocytes have to be activated For practical use, points 4 and 6 are not very important. However, points 1 to 3 require extensive screening measures, make storage difficult or incur losses of material and make the use of automatic pipetting equipment appear critical. The most serious disadvantage, however, is that the method cannot be used in the presence of plasma because of the high fibrinogen content, since plasma fibrinogen inhibits the binding of $^{125}$I-fibrinogen to activated platelets with an $IC_{50}$ of 120 nM. Therefore, washed or gel-filtered thrombocytes have to be used to measure the binding (see Harfenist, E. J. et al., Blood 71: 132–136 (1988)).

It has now, surprisingly, been found that there are fibrinogen receptor antagonists which bind to the fibrinogen receptor even in the presence of plasma-fibrinogen. Such fibrinogen receptor antagonists are described for example in EP-A-372486 and in EP-A-381033 and in the not previously published German or European Published Applications EP-A-483667 (Case 5/1054), EP-A-496378 (Case 5/1056), EP-A-503548 (Case 5/1068), EP-A-525629 (Case 5/1074), EP-A-528369 (Case 5/1075), DE-A-4129603 (Case 5/1076) and DE-A-4134467 (Case 5/1077).

Preferred fibrinogen receptor antagonists are the amidines of general formula $$R_a-R_b \tag{I}$$

wherein $R_a$ denotes a 4-amidinophenyl or 5-amidino-pyrimid-2-yl group and denotes an HOOC—D—C—B—A— group, wherein A denotes an optionally methoxy-substituted phenylene group in which, additionally, one or two methine groups may be replaced by a nitrogen atom, or A denotes an imidazolinon-di-yl, imidazolidinon-di-yl, imidazolidin-dion-di-yl, triazolinon-di-yl or 1,1-dioxo-3,4-dihydro-1,2,5-thiadiazolidin-di-yl group each optionally substituted at a carbon atom by a methyl, ethyl or trifluoromethyl group, or A denotes a benzimidazol-di-yl group optionally substituted by the group $R_1$ at one of the nitrogen atoms, or A denotes an aminocarbonyl group bound to the group B by the nitrogen atom, B denotes a methylene, carbonyl, cyclohexylene, phenylene or imidazol-di-yl group, an aminocarbonyl group bound to the group C via the nitrogen atom, which may simultaneously be substituted by a methyl group at the nitrogen atom, or a methyleneoxy group bound to the group A via the oxygen atom, C denotes an ethylene group optionally substituted by the group $R_2$, a cyclohexylene group, a pyrrolidin-di-yl or pyrrolidinon-di-yl group optionally substituted by the group $R_3$ at the nitrogen atom, a piperidin-di-yl group or an aminocarbonyl group bound to the group D via the nitrogen atom and D denotes a bond or a methylene or ethylene group, whilst $R_1$ denotes a methyl, 2-piperazinoethyl, 2-(3,4-dimethoxyphenyl)ethyl or 3-thiomorpholinopropyl group, $R_2$ denotes an amino or hydroxy group and $R_3$ denotes a 3-phenylpropyl, acetyl, methanesulphonyl or pyrrolidinocarbonylmethyl group, particularly those fibrinogen receptor antagonists wherein $R_a$ denotes a 4-amidino-phenyl group or, if $R_b$ denotes a phenyl group substituted in the 4-position by a 3-carboxymethyl-pyrrolidin-2-on-5-yl-methyloxy group, $R_a$ may also denote a 5-amidino-pyrimid-2-yl group and $R_b$ denotes a phenyl group which is substituted in the 4-position by a 4-carboxymethyl-pyrrolidin-2-yl-methyloxy, 3-carboxymethyl-pyrrolidin-2-on-5-yl-methyloxy, 4-carboxymethyl-piperidinomethyl, 4-carboxymethyl-piperidinocarbonyl, 4-carboxycyclohexylaminocarbonyl or N-methyl-N-(4-carboxycyclohexyl)-aminocarbonyl group, whilst in the 1-position each pyrrolidine moiety may be substituted by an acetyl or methanesulphonyl group and the pyrrolidinone moiety may be substituted by a 3-phenyl-propyl or pyrrolidinocarbonylmethyl group, a 4-methoxy-phenyl group substituted in the 3-position by a 4-carboxycyclohexyl-aminocarbonyl group, a pyridazin-3-yl group substituted in the 6-position by an imidazol-1-yl group, wherein the imidazolyl moiety is substituted in the 4-position by a 2-amino-2-carboxy-ethyl or 2-carboxy-2-hydroxy-ethyl group, an imidazolidin-2-on-1-yl group substituted in the 3-position by a 4-(2-carboxyethyl)-cyclohexyl or 4-(2-carboxyethyl)phenyl group, a 4-methyl-4-imidazolin-2-on-1-yl or imidazolidin-2,4-dion-1-yl group substituted in the 3-position by a 4-(2-carboxyethyl)-phenyl group, a 1,2,4-triazol-5-in-3-on-2-yl group optionally methyl- or ethyl-substituted in the 5-position and substituted in the 4-position by a 4-(2-carboxyethyl)-phenyl group, a 1,2,4-triazol-5-in-3-on-4-yl group substituted in the 2-position by a 4-(2-carboxyethyl)-phenyl group, a 1,1-dioxo-1,2,5-thiadiazolidin-2-yl group substituted in the 5-position by a 4-(2-carboxyethyl)-phenyl group, a benzimidazol-2-yl group optionally substituted in the 1-position by a methyl, 2-piperazino-ethyl or 2-(3,4-dimethoxyphenyl)-ethyl group and substituted in the 5-position by a 2-carboxyethylaminocarbonyl group, or a phenylaminocarbonyl group substituted in the 3-position by a 2-carboxyethylaminocarbonyl group, the tautomers thereof, the stereoisomers thereof including mixtures and the salts thereof.

However, particularly preferred are those compounds of general formula I above which have a good in vitro activity in the collagen-induced aggregation test, the tritium-labelled fibrinogen receptor antagonists according to the invention showing an EC=activity of less than 500 nM in this test (see Huang, E. M. and Detwiler, T. C.: "Stimulus-Response Coupling Mechanisms" in Biochemistry of Platelets, Academic Press, Orlando, Fla. 1986, pages 1–68), and especially the compounds (1) (3S,5S)- and (3R,5R)-5-[[(4-(5-amidinopyrimid-2-yl) phenyl]-oxymethyl]-3-carboxymethyl-pyrrolidin-2-one, (2) (3S,5S)- and (3R, 5R)-1-acetyl-5-[(4'-amidino-4-biphenylyl)-oxymethyl]-3-carboxymethyl-pyrrolidine, (3) (3S,5S)- and (3R,5R)-5-[(4'-amidino-4-biphenylyl)-oxymethyl]-3-carboxymethyl-1-methanesulphonyl-pyrrolidine, (4) (3S,5S)- and (3R,5R)-5-[(4'-amidino-4-biphenylyl)-oxymethyl]-3-carboxymethyl-pyrrolidin-2-one, (5) 4-amidino-4'-[(trans-4-carboxycyclohexyl)-aminocarbonyl]-biphenyl, (6) 4-amidino-4'-[N-(trans-4-carboxycyclohexyl)-N-methyl-aminocarbonyl]-biphenyl, (7) 1-(4-amidinophenyl)-3-[4-(2-carboxyethyl)-phenyl]-imidazolidin-2,4-dione, (8) 1-(4-amidinophenyl)-3-[4-(2-carboxyethyl)-phenyl]-4-methyl-4-imidazolin-2-one, (9) 2-(4-amidinophenyl)-4-[4-(2-carboxyethyl)-phenyl]-1,2,4-triazol-5-in-3-one, (10) 4-(4-amidinophenyl)-2-[4-(2-carboxyethyl)-phenyl]-1,2,4-triazol-5-in-3-one, (11) 2-(4-amidinophenyl)-4-[4-(2-carboxyethyl)-phenyl]-5-methyl-1,2,4-triazol-5-in-3-one, (12) 2-(4-amidinophenyl)-4-[4-(2-carboxyethyl)-phenyl]-5-ethyl-1,2,4-triazol-5-in-3-one, (13) 2-(4-amidinophenyl)-5-[4-(2-carboxyethyl)-phenyl]-1,2,5-thiadiazolidin-1,1-dioxide, (14) 1-(4-amidinophenyl)-3-[4-(2-carboxyethyl)-cyclohexyl]-imidazolidin-2-one, (15) 2-(4-amidinophenyl)-5-[(2-carboxyethyl)-aminocarbonyl]-1-[2-(piperazin-1-yl)-ethyl]-benzimidazole, (16) 4-amidino-4'-[4-(carboxymethyl)-piperidinocarbonyl]-biphenyl and the salts thereof.

Particularly preferred compounds are (1) (3S,5S)- and (3R,5R)-5-[[(4-(5-amidinopyrimid-2-yl)-phenyl]-oxymethyl]-3-carboxymethyl-pyrrolidin-2-one, (2) (3S,5S)- and (3R,5R)-1-acetyl-5-[(4'-amidino-4-biphenylyl)-oxymethyl]-3-carboxymethyl-pyrrolidine, (3) (3S,5S)- and (3R,5R)-5-[(4'amidino-4-biphenylyl)-oxymethyl]-3-carboxymethyl-1-methanesulphonyl-pyrrolidine, (4) (3S,5S)- and (3R,5R)-5-[(4'-amidino-4-biphenylyl)-oxymethyl]-3-carboxymethyl-pyrrolidin-2-one, (5) 4-amidino-4'-[4-(carboxymethyl)-piperidinocarbonyl]-biphenyl and the salts thereof.

The above-mentioned fibrinogen receptor antagonists of general formula I have an affinity for the receptor which is comparable to or greater than that of $^{125}$I-fibrinogen. Their binding to the receptor is not disrupted by foreign proteins. Therefore, if at least one atom therein is replaced by a detectable atom, e.g. if a hydrogen atom is replaced by a tritium atom, they can be used as ligands in the fibrinogen receptor binding test, even in the presence of plasma.

The present invention thus relates to the new tritium-labelled fibrinogen receptor antagonists which have an affinity for the receptor comparable to or greater than that of $^{125}$I-fibrinogen and whose binding is not disrupted by foreign proteins, especially the compounds of general formula I above which have an affinity ($K_D$) of less than 500 nM in relation to the receptor, in the presence of foreign protein, e.g. albumin or fibrinogen, their use as ligands a) to determine the binding of chemical substances to fibrinogen receptors and b) to determine the concentration of fibrinogen receptor antagonists particularly in the presence of foreign albumin and/or in different body fluids such as blood plasma or urine, and processes for preparing them.

The fibrinogen receptor binding test according to the invention was carried out, for example, using (3S,5S)-5-[(4'-amidino-4-biphenylyl)-oxymethyl]-3-carboxymethyl-pyrrolidin-2-one-[3-$^3$H-4-biphenylyl][=$^3$H-BIBU 52 ZW] as ligand in the following manner:

A suspension of human thrombocytes in plasma is incubated with $^3$H-BIBU 52 and varying concentrations of the substance to be tested. The free and bound ligand is separated off by centrifuging and quantitatively determined by scintillation counting. The inhibition of the $^3$H-BIBU 52 binding by the test substance is determined from the measurements obtained.

Figure 1:
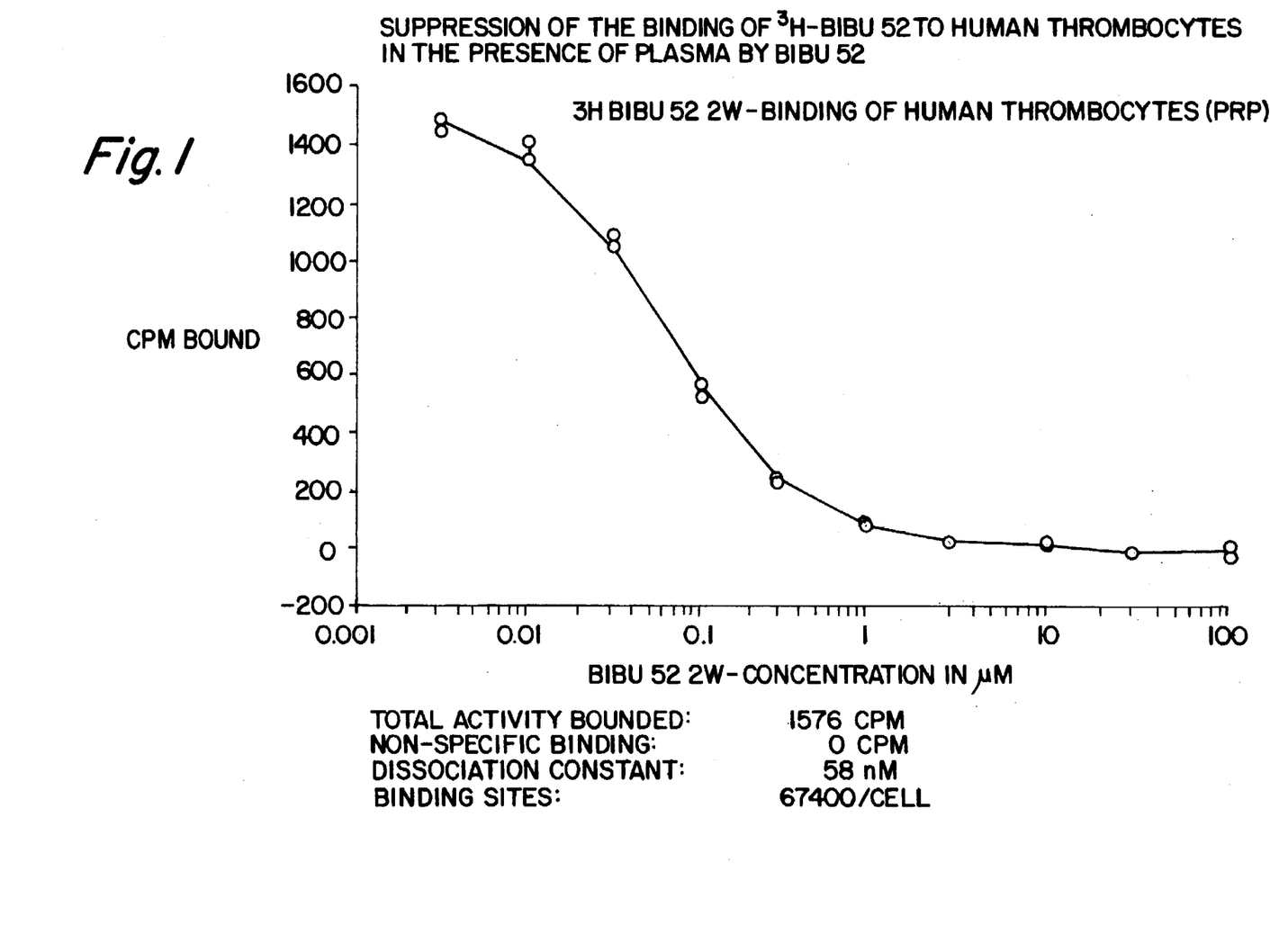
FIG. 1 depicts the supression of binding of tritiated BIBU 52 (according to the instant invention) to human thromobocytes in the presence of plasma BIBU 52.

In order, for example, to measure the competition of binding of $^3$H-BIBU 52 by non-labelled BIBU 52, blood is taken from an anticubital vein and anticoagulated with trisodium citrate (final concentration 13 mM). The blood is centrifuged for 10 minutes at 170 ×g and the supernatant platelet-rich plasma (PRP) is removed. The remaining blood is sharply centrifuged once more in order to obtain plasma. The PRP is diluted with autologous plasma 1:10. 750 µl are incubated for 20 minutes at ambient temperature with 50 µl of physiological saline solution, 100 µl of test substance solution, 50 µl of $^{14}$C-sucrose and 50 µl of $^3$H-BIBU 52. In order to measure the non-specific binding, 30 µM of BIBU 52 are used instead of the test substance. The samples are centrifuged for 20 seconds at 10000 ×g and the supernatant is drawn off. 100 µl thereof are measured in order to determine the free ligand. The pellet is dissolved in 500 µl of 0.2N NaOH, 450 µl are mixed with 25 µl of 5N HCl and measured. The residual plasma remaining in the pellet is determined from the $^{14}$C-content and the bound ligand is determined from the $^3$H-measurement. After the non-specific binding has been substracted, the pellet activity is plotted against the concentration of the test substance (see FIG. 1) and the concentration for 50% inhibition of binding is determined.

The new tritium-labelled fibrinogen receptor antagonists are obtained by methods known from the literature, e.g.

a) by catalytic tritiation of an unsaturated carbon-carbon bond with tritium, b) by hydrogenolytic exchange of a halogen atom e.g. a chlorine, bromine or iodine atom, against tritium, c) by catalytic hydrogen/tritium exchange with tritium, d) by catalytic hydrogen/tritium exchange in tritiated solvents or e) by tritiation of a precursor of the fibrinogen receptor antagonist to be produced, followed by synthesis of the fibrinogen receptor antagonist.

Process a) is conveniently carried out in a solvent such as methanol or ethanol, but preferably in a non-polar solvent such as cyclohexane, dioxane, tetrahydrofuran, ethyl acetate or dimethylsulphoxide, in the presence of a suitable catalyst such as palladium/activated charcoal, palladium black, platinum/activated charcoal, Raney nickel or mixtures of platinum and rhodium, ruthenium, osmium or iridium on activated charcoal with tritium gas, expediently at ambient temperature and under normal pressure until the uptake of gas has ceased. Then, in order to remove the labile tritium, the catalyst is filtered off, the solvent is removed, the residue is taken up in a polar solvent, refluxed for 10 minutes and the solvent is drawn off again after 12 hours at ambient temperature.

Process b) is preferably carried out in a suitable solvent such as water, methanol, ethanol, dimethylformamide or dimethylsulphoxide, but preferably in a non-polar solvent such as ethyl acetate, dioxane or tetrahydrofuran, in the presence of a suitable catalyst such as 5% palladium on activated charcoal, 10% palladium on activated charcoal, palladium, platinum, palladium dichloride, 2% palladium on barium carbonate, palladium/barium sulphate or Raney nickel, with the addition of an excess of a basic component such as triethylamine, pyridine, quinoline, sodium hydroxide, potassium carbonate, ammonia, magnesium oxide or calcium oxide, with tritium gas at 1 to 5 bar and at 20 to 50° C., preferably at 25° C. Then, in order to remove the labile tritium, the catalyst is filtered off, the solvent is removed, the residue is taken up in a polar solvent, refluxed for 10 minutes and the solvent is removed once more after 12 hours at ambient temperature.

Process c) is preferably carried out in a suitable solvent such as phosphate buffer pH 7, water, glacial acetic acid, methanol or ethanol, in the presence of a suitable catalyst such as palladium dioxide/barium sulphate, platinum, palladium, 5% palladium on activated charcoal, 10% palladium on activated charcoal, platinum dioxide hydrate or palladium/platinum dioxide hydrate, by stirring under carrier-free tritium gas within a period of from one hour to 20 days at 20 to 50° C., preferably at 25° C. Then, in order to remove the labile tritium from the catalyst, it is filtered off, the solvent is removed, the residue is taken up in a polar solvent, refluxed for 10 minutes and after 12 hours at ambient temperature the solvent is again removed and the resulting product is purified by HPLC.

Process d) is carried out in a suitable tritiated solvent such as HTO, 70% $CH_3COOT$, $CF_3COOT$, KOH/HTO, dioxane/HTO, $HTSO_4$/HTO/water, $CH_3T$ or $CH_3CH_2OT$, in the presence of a suitable catalyst such as platinum dioxide, 5% palladium on activated charcoal, 10% palladium on activated charcoal, palladium, platinum or Raney nickel, by heating in a sealed vessel for one to 20 hours to 100° to 140° C. Then in order to remove the labile tritium, the catalyst is filtered off, the solvent is removed, the residue is taken up in a polar solvent, refluxed for 10 minutes and after 12 hours at ambient temperature the solvent is again removed and the resulting product is purified by HPLC.

The precursors for preparing tritiated fibrinogen receptor antagonists according to process e) are prepared by conventional chemical methods, in which the labelled intermediate required is prepared according to processes a) to d), but preferably according to process a).

In the reactions described hereinbefore, it is particularly advantageous to use, instead of the free carboxylic acid, the esters thereof with a lower alcohol, e.g. the methyl, ethyl, n-propyl, isopropyl or tert.butylesters, particularly the methylester. After tritiation the ester is then converted into the corresponding free carboxylic acid by hydrolysis, preferably in the presence of a base such as sodium hydroxide solution, e.g. in the presence of methanol/2N sodium hydroxide solution (6:1) at ambient temperature.

Particularly advantageously, the compounds

[$^3$H]1-(4-amidinophenyl)-3-[4-(2-carboxyethyl)-cyclohexyl]-imidazolidin-2-one, starting from 1-(4-amidinophenyl)-3-[4-(2-carboxyethyl)-cyclohexyl]-4-imidazolin-2-one,

[$^3$H]1-(4-amidinophenyl)-3-[4-(2-carboxyethyl)-phenyl]-imidazolidin-2,4-dione, starting from 1-(4-amidinophenyl)-3- [4-(2-carboxyethenyl)-phenyl]-imidazolidin-2,4-dione and

[$^3$H]2-(4-amidinophenyl)-5-[4-(2-carboxyethyl)-phenyl]-1,2,5-thiadiazolidin-1,1-dioxide, starting from 2-(4-amidino-phenyl)-5-[4-(2-carboxyethenyl)-phenyl]-1,2,5-thiadiazol-1,1-dioxide, are obtained by catalytic hydrogenation according to process a) in methanol or dimethylsulphoxide with tritium gas using 10% palladium on activated charcoal as catalyst, the compounds

[$^3$H](3S,5S)- and (3R,5R)-5-[[(4-(5-amidinopyrimid-2-yl)-phenyl]-oxymethyl]-3-carboxymethyl-pyrrolidin-2-one,

[$^3$H](3S, 5S )- and (3R, 5R)-1-acetyl-5-[(4'-amidino-4-biphenylyl)-oxymethyl]-3 -carboxymethyl-pyrrolidine,

[$^3$H](3S, 5S )- and (3R, 5R)-5-[(4'-amidino-4-biphenylyl)-oxymethyl]-3-carboxymethyl-1-methanesulphonyl-pyrrolidine,

[$^3$H](3S,5S)- and (3R,5R)-5-[(4'-amidino-4-biphenylyl)-oxymethyl]-3-carboxymethyl-pyrrolidin-2-one,

[hu 3H]4-amidino-4'-[(trans-4-carboxycyclohexyl)-aminocarbonyl]-biphenyl,

[$^3$H]4-amidino-4'-[N-(trans-4-carboxycyclohexyl)-N-methyl-aminocarbonyl]-biphenyl,

[$^3$H]4-amidino-4'-[4-(carboxymethyl)-piperidinocarbonyl]-biphenyl and

[3H]2-(4-amidinophenyl)-5-[(2-carboxyethyl)-aminocarbonyl]-1-[2-(piperazin-1-yl)-ethyl]-benzimidazole, are obtained by hydrogenolytic exchange of halogen for tritium according to process b) in a sealed vessel in dimethylformamide with vigorous stirring under an ambient pressure of 370 GBq of carrier-free tritium gas, the compounds

[$^3$H]4-amidino-4'-[(trans-4-carboxycyclohexyl)-aminocarbonyl]-biphenyl,

[$^3$H]4-amidino-4'-[4-(carboxymethyl)-piperidinocarbonyl]-biphenyl and

[$^3$H]4-amidino-4'-[N-(trans-4-carboxycyclohexyl)-N-methyl-aminocarbonyl]-biphenyl are obtained by catalytic hydrogen/tritium exchange in a tritiated solvent according to process d) by 20-hours treatment of the non-tritiated compound in dioxane/HTO (1:1) in the presence of platinum dioxide at 100° C.,
the compounds

[³H]1-(4-amidinophenyl)-3-[4-(2-carboxyethyl)-phenyl]-4-methyl-4-imidazolin-2-one,

[³H]2-(4-amidinophenyl)-4-[4-(2-carboxyethyl)-phenyl]-1,2,4-triazol-5-in-3-one,

[³H]4-(4-amidinophenyl)-2-[4-(2-carboxyethyl)-phenyl]-1,2,4-triazol-5-in-3-one,

[³H]2-(4-amidinophenyl)-4-[4-(2-carboxyethyl)-phenyl]-5-methyl-1,2,4-triazol-5-in-3-one and

[³H]2-(4-amidinophenyl)-4-[4-(2-carboxyethyl)-phenyl]-5-ethyl-1,2,4-triazol-5-in-3-one, are obtained by tritiation of a precursor of the fibrinogen receptor antagonist which is to be produced with subsequent synthesis of the fibrinogen receptor antagonist according to process e), preferably by treating a solution of a correspondingly substituted methyl 4-amino-cinnamate in ethyl acetate with 370 GBq of carrier-free tritium gas in the presence of 10% palladium on activated charcoal and subsequent reaction by known methods to obtain the 1,2,4-triazol-5-in-3-ones or 4-imidazolin-2-ones, the methylesters preferably obtained in this way subsequently being hydrolysed at ambient temperature with methanol/2N sodium hydroxide solution.

The compounds (3S,5S)-5-[(4'-amidino-4-biphenylyl)-oxymethyl]-3-carboxymethyl-pyrrolidin-2-one[3-³H-4-biphenylyl] and (3R,5R)-5-[(4'-amidino-4-biphenylyl)-oxymethyl]-3-carboxymethyl-pyrrolidin-2-one[3-³H-4-biphenylyl] are preferably obtained according to process b) by hydrogenolytic exchange of a halogen atom in the 3-position of the biphenyl nucleus, preferably the bromine atom.

The Examples which follow are intended to illustrate the invention:

Preparation of the starting compounds:

EXAMPLE A

3-Bromo-4'-cyano-4-hydroxybiphenyl 3.9 g of 4'-cyano-4-hydroxybiphenyl are dissolved in 250 ml of chloroform at boiling temperature. To this solution 1 ml of bromine in 20 ml of chloroform is added dropwise whilst refluxing continues. The colourless solution is cooled and evaporated under reduced pressure.

Yield: 5.48 g (100% of theory),

Melting point: 186°–189° C.

$R_f$ value: 0.66 (silica gel; 1,2-dichloroethane/ethyl acetate =9:1)

| Calc.: | C | 56.96 | H | 2.94 | N | 5.11 | Br | 29.15 |
|---|---|---|---|---|---|---|---|---|
| Found: |  | 57.07 |  | 3.15 |  | 5.03 |  | 29.14 |

EXAMPLE B (S)-1-(Benzyloxycarbonyl)-5-[(trityloxy)methyl]-2-pyrrolidinone

A solution of 160 g of (S)-5-[(trityloxy)methyl]-2-pyrrolidinone in 1600 ml of dry tetrahydrofuran is mixed with 179 ml of a 2.5-molar solution of butyl lithium in hexane within 35 minutes at −65° C. After 10 minutes, at −65° C., a solution of 66.8 ml of benzyl chloroformate in 100 ml of dry tetrahydrofuran is added dropwise and the mixture is stirred for one hour. Then 200 ml of saturated saline solution are added and the tetrahydrofuran is evaporated off. The residue is distributed between 3.5 litres of ethyl acetate and 200 ml of water, the organic phase is separated off and washed twice with water and saline solution. The organic phase is separated off, dried and evaporated under reduced pressure. The crude product is recrystallised from a little ethanol.

Yield: 181 g (82% of theory),

Melting point: 103°–105° C.

$R_f$ value: 0.53 (silica gel; cyclohexane/ethyl acetate=2:1)

| Calc.: | C | 78.19 | H | 5.95 | N | 2.85 |
|---|---|---|---|---|---|---|
| Found: |  | 78.34 |  | 6.00 |  | 3.10 |

EXAMPLE C (3S,5S)-1-(Benzyloxycarbonyl)-3-[(methoxycarbonyl)-methyl]-5-[(trityloxy)methyl]-2-pyrrolidinone To a solution of 40.0 g of (S)-1-(benzyloxycarbonyl)-5-[(trityloxy)methyl]-2-pyrrolidinone in 400 ml of anhydrous tetrahydrofuran are added dropwise at −65° C., within 20 minutes and with stirring, 81.3 ml of a 1-molar solution of lithium-hexamethyldisilazide in tetrahydrofuran. After 10 minutes stirring at this temperature a solution of 7.5 ml of methyl bromoacetate in 50 ml of anhydrous tetrahydrofuran is added dropwise within 30 minutes. After a further 45 minutes stirring at −65° C. the reaction solution is allowed to warm up to 0° C. and 20 ml of saturated saline solution are added. The solvent is evaporated off in vacuo and the residue remaining is taken up in 750 ml of ethyl acetate. The organic phase is extracted three times with water and once with saturated saline solution, dried over magnesium sulphate and evaporated under reduced pressure in vacuo. The crude product is chromatographed with cyclohexane/ethyl acetate (2:1) over silica gel.

Yield: 31.8 g (70% of theory), $R_f$ value: 0.54 (silica gel; cyclohexane/ethyl acetate=2:1)

| Calc.: | C | 74.58 | H | 5.90 | N | 2.49 |
|---|---|---|---|---|---|---|
| Found: |  | 74.61 |  | 6.09 |  | 2.43 |

EXAMPLE D (3S,5S)-5-Hydroxymethyl-3-[(methoxycarbonyl)methyl]-2-pyrrolidinone 70.6 g of (3S,5S)-1-(benzyloxycarbonyl)-3-[(methoxycarbonyl)-methyl]-5-[(trityloxy)methyl]-2-pyrrolidinone in 700 ml of methanol are hydrogenated for 3.5 hours at 50° C. under a hydrogen pressure of 5 bar with 7 g of a catalyst consisting of 10% palladium on activated charcoal. Then the catalyst is filtered off and the filtrate is evaporated under reduced pressure. The residue is stirred twice with 150 ml of petroleum ether and the petroleum ether phase is decanted off. The remaining oil is chromatographed over silica gel with methylene chloride/methanol (10:1).

Yield: 17.0 g of yellowish oil (73% of theory), $R_f$ value: 0.36 (silica gel; methylene chloride/methanol= 10:1)

EXAMPLE E (3S,5S)-5-[(Methanesulphonyloxy)methyl]-3-[(methoxycarbonyl)-methyl]-2-pyrrolidinone To a solution of 8.0 g of (3S,5S)-5-hydroxymethyl-3-[(methoxycarbonyl)methyl]-2-pyrrolidinone and 4.95 ml of methanesulphonic acid chloride in 100 ml of methylene chloride, a solution of 9.0 ml of triethylamine in 15 ml of methylene chloride is added dropwise at 0° C. within 15 minutes. The mixture is stirred for one hour at 0° C. and for a further hour at ambient temperature. After the addition of 20 ml of water the organic phase is separated off and washed twice with water. The organic phase is dried over magnesium sulphate and evaporated under reduced pressure in vacuo. The crude product is chromatographed with ethyl acetate/methanol (15:1) over silica gel and the solid obtained is recrystallised from methyl tert.butylether/acetone.

Yield: 6.8 g (60% of theory),

Melting point: 85°–87° C.

$R_f$ value: 0.42 (silica gel; acetone/petroleum ether=4:1)

| | C | H | N | S |
|---|---|---|---|---|
| Calc.: | 40.75 | 5.70 | 5.28 | 12.09 |
| Found: | 40.63 | 5.50 | 5.45 | 12.01 |

EXAMPLE F

4:1 Mixture of (3S,5S)- and (3R,5S)-5-[(3-bromo-4'-cyano-4-biphenylyl)oxymethyl]-3-[(methoxycarbonyl)-methyl]-2-pyrrolidinone A suspension of 7.0 g of 3-bromo-4'-cyano-4-hydroxybiphenyl and 10.5 g of caesium carbonate in 150 ml of dimethylformamide is stirred for one hour at ambient temperature. After the addition of 7.6 g of (3S,5S)-5-[(methanesulphonyloxy)methyl]-3-[(methoxycarbonyl)-methyl]-2-pyrrolidinone the mixture is stirred for 2 days at 55° C. Then the solvent is substantially evaporated off and the residue is mixed with saline solution and dilute hydrochloric acid. The aqueous phase is extracted with ethyl acetate, the organic phase is dried over sodium sulphate and evaporated under reduced pressure. The crude product is chromatographed with ethyl acetate over silica gel.

Yield: 7.4 g (65% of theory), $R_f$ value: 0.51 (silica gel; methylene chloride/methanol= 15:1)

| | C | H | N | Br |
|---|---|---|---|---|
| Calc.: | 56.90 | 4.32 | 6.32 | 18.03 |
| Found: | 56.58 | 4.41 | 6.17 | 17.92 |

EXAMPLE G (3S,5S)-5-[(4'-amidino-3-bromo-4-biphenylyl)oxymethyl]-3-[(methoxycarbonyl)methyl]-2-pyrrolidinone-hydrochloride At 0° C., with stirring, hydrogen chloride is piped into a solution of 6.4 g of the 4:1 mixture of (3S,5S)- and (3R,5S)-5-[(3-bromo-4'-cyano-4-biphenylyl)oxymethyl]-3-[(methoxycarbonyl)methyl]-2-pyrrolidinone in 250 ml of anhydrous methanol for 2 hours. After 2 hours stirring at ambient temperature the solvent is evaporated off in vacuo at a bath temperature of 30° C. The residue is dissolved in 250 ml of anhydrous methanol and after the addition of 20 g of ammonium carbonate it is stirred for 16 hours at ambient temperature. The suspension is filtered over a little silica gel and the filtrate is evaporated under reduced pressure in vacuo. The crude product is chromatographed with methylene chloride/methanol/conc. ammonia (4:1:0.25) over silica gel. The isomerically pure product is obtained in the form of the hydrochloride as the last fraction.

Yield: 270 mg (4% of theory), $R_f$ value: 0.16 (silica gel; methylene chloride/methanol/conc. ammonia=4:1:0.25)

EXAMPLE H (3S,5S)-5-[[4-(5-Amidino-2-pyridyl)phenyl]oxymethyl]-3-[(tert.butyloxycarbonyl)methyl]-2-pyrrolidinone-hydrochloride 2.1 g of (3S,5S)-3-[(tert.butyloxycarbonyl)methyl]-5-[[4-(5-cyano-2-pyridyl)phenyl]oxymethyl]-Z-pyrrolidinone in 50 ml of dry methanol are stirred with 8.5 ml of 0.13M sodium methoxide solution for 40 hours at ambient temperature. 63 µl of glacial acetic acid followed by 0.5 g of ammonium chloride are added and the mixture is stirred for 2½ days at ambient temperature. After it has been evaporated under reduced pressure, it is purified by column chromatography on silica gel with methylene chloride/methanol (6:1).

Yield: 1 g (42% of theory),

Melting point: 207° C. (decomp.)

$R_f$ value: 0.56 (silica gel; methylene chloride/methanol= 4:1)

The following compound is obtained analogously:

(3S,5S)-5-[[4-(5-amidino-2-pyrimidyl)phenyl]oxymethyl]-3-[(tert.butyloxycarbonyl)methyl]-2-pyrrolidinone-hydrochloride Melting point: 277°–279° C. (decomp.)

$R_f$ value: 0.38 (reversed phase silica gel; methanol/5% aqueous saline solution=6:4)

EXAMPLE I (3S,5S)-5-[(4'-amidino-4-biphenylyl)oxymethyl]-3-[(methoxycarbonyl)methyl]-1-(3-phenylpropyl)-2-pyrrolidinone-hydrochloride-semihydrate 140 g of (3S,5S)-5-[(4'-cyano-4-biphenylyl)oxymethyl]-3-[(methoxycarbonyl)methyl]-1-(3-phenylpropyl)-2-pyrrolidinone are dissolved in 1100 ml of methanol and cooled to –20° C. At this temperature hydrochloric acid gas is piped in for 4 hours with stirring and the mixture is stirred for a further 16 hours at ambient temperature. The solvent is evaporated off in vacuo, leaving the crude iminoester hydrochloride as a viscous oil (172 g). This crude product is dissolved in 1500 ml of methanol and after the addition of 144 g of ammonium carbonate it is stirred for 2 hours at ambient temperature. Then a further 48 g of ammonium carbonate are added and the mixture is stirred for a further 1½ hours. The reaction mixture is adjusted to pH 3.5 with methanolic hydrochloric acid with stirring. It is evaporated under reduced pressure to about 800 ml in vacuo and the ammonium chloride precipitated is filtered off. The filtrate is then evaporated further until crystallisation begins (down to about 350 ml). After crystallisation has ended the precipitate is filtered off and washed with 75 ml of ice cold methanol and finally with acetone and ether. By concentrating the filtrates another fraction can be obtained. Both sets of crystals are combined and recrystallised from methanol.

Yield: 128.7 g (83% of theory),
Melting point: 184°–187° C. (decomp.)

| Calc.: | C | 66.11 | H | 6.47 | N | 7.71 | Cl | 6.50 |
|---|---|---|---|---|---|---|---|---|
| Found: | | 65.98 | | 6.41 | | 7.67 | | 6.67 |

The following are obtained analogously:

(1) (3S,5S)-5-[(4'-amidino-4-biphenylyl)oxymethyl]-3-[(methoxycarbonyl)methyl]-2-pyrrolidinone ×1.25 HCl
Melting point: from 141° C. (decomp.)
$R_f$ value: 0.30 (silica gel; methylene chloride/methanol= 85:15)

| Calc.: | C | 59.07 | H | 5.72 | N | 9.84 | Cl | 10.38 |
|---|---|---|---|---|---|---|---|---|
| Found: | | 58.96 | | 5.96 | | 9.68 | | 10.10 |

(2) (3S,5S)-1-acetyl-5-[(4'-amidino-4-biphenylyl)-oxymethyl]- 3-[(methoxycarbonyl)methyl]-pyrrolidine-hydrochloride
$R_f$ value: 0.16 (silica gel; methylene chloride/methanol= 10:1)

| Calc.: | C | 61.95 | H | 6.33 | N | 9.42 | Cl | 7.95 |
|---|---|---|---|---|---|---|---|---|
| Found: | | 61.76 | | 6.31 | | 9.11 | | 7.84 |

(3) (3R, 5R)-5-[(4'-amidino-4-biphenylyl)oxymethyl]-3-[(methoxycarbonyl)methyl]-2-pyrrolidinone-hydrochloride-semihydrate
Melting point: 138° C. (decomp.)
$R_f$ value: 0.52 (reversed phase silica gel (RP8); methanol/ 10% aqueous saline solution=6:4)

| Calc.: | C | 59.08 | H | 5.90 | N | 9.84 | Cl | 8.31 |
|---|---|---|---|---|---|---|---|---|
| Found: | | 58.96 | | 6.19 | | 9.68 | | 8.93 |

(4) (3S,5S)-5-[(4'-amidino-4-biphenylyl)oxymethyl]-3-[(methoxycarbonyl)methyl]-1-[(pyrrolidine-N-carbonyl)methyl]-2-pyrrolidinone-hydrochloride
$R_f$ value: 0.46 (silica gel; methylene chloride/methanol/ conc. aqueous ammonia=30:10:2)

(5) (3S,5S)-5-[(4'-amidino-4-biphenylyl)oxymethyl]-1-methanesulphonyl-3-[(methoxycarbonyl)methyl]-pyrrolidine-hydrochloride
$R_f$ value: 0.24 (silica gel; methylene chloride/methanol= 10:1)

| Calc.: | C | 54.82 | H | 5.85 | N | 8.72 | Cl | 7.36 |
|---|---|---|---|---|---|---|---|---|
| Found: | | 54.68 | | 5.82 | | 8.47 | | 7.20 |

EXAMPLE J

1-[6-(4-Amidino-phenyl)-3-pyridazinyl]-4-(2-methoxycarbonyl-ethyl)-imidazole

A mixture of 1.1 g of 1-[6-(4-cyano-phenyl)-3-pyridazinyl]-4-(2-methoxycarbonyl-ethyl)-imidazole, 1500 ml of absolute methanol and 50 ml of methylene chloride is saturated with stirring and ice-cooling with dry hydrogen chloride. The mixture is stirred for a further 16 hours at ambient temperature and the solvent is distilled off in vacuo. The residue is taken up in 250 ml of absolute methanol and combined with 8 g of ammonium carbonate. It is stirred for 30 minutes at ambient temperature, the precipitate is removed by suction filtering and the filtrate is evaporated under reduced pressure in vacuo. The evaporation residue is combined with the precipitate obtained previously and purified by column chromatography (eluant: methylene chloride/methanol/conc. ammonia=2:1:0.25).

Yield: 0.36 g (31% of theory),
$R_f$ value: 0.22 (silica gel; methylene chloride/methanol/ conc. ammonia=2:1:0.25)

The following compounds are obtained analogously:

(1) 1-[6-(4-amidino-phenyl)-3-pyridazinyl]-4-(2-hydroxy-2-methoxycarbonyl-ethyl)-imidazole
$R_f$ value: 0.17 (silica gel; methylene chloride/methanol/ conc. ammonia=2:1:0.25)

(2) 1-[6-(4-amidino-phenyl)-3-pyridazinyl]-4-(2-amino-2-methoxycarbonyl-ethyl)-imidazole-tris-trifluoroacetate
The starting product used is 1-[6-(4-cyano-phenyl)-3-pyridazinyl]-4-(2-tert.butyloxycarbonylamino-2-methoxycarbonyl-ethyl)-imidazole The crude free base is converted into the tris-trifluoroacetate by taking up in methylene chloride, mixing with trifluoroacetic acid, concentration and purification over silica gel (eluant: methylene chloride/methanol/conc. ammonia=2:1:0.25).
$R_f$ value: 0.18 (silica gel; methylene chloride/methanol/ conc. ammonia=2:1:0.25)

EXAMPLE K

4-Amidino-4,-(5-methoxycarbonyl-pentyloxy)-biphenyl ×0.5 $H_2CO_3$ 75 ml of methanol are covered with 30 ml of petroleum ether and hydrogen chloride gas is piped in, whilst cooling with ice, until saturation is reached. Then 2.1 g of 4-cyano-4'-(5-ethoxycarbonyl-pentyloxy)-biphenyl are added and the mixture is stirred for 18 hours at ambient temperature. It is evaporated to dryness in vacuo, the residue is suspended in methanol, 5.36 g of ammonium carbonate are added and the mixture is stirred for 16 hours at ambient temperature. The precipitate obtained is filtered off and purified by stirring with methylene chloride/methanol (85:15) and water.

Yield: 1.75 g (75% of theory),
Melting point: 185°–189° C. (decomp.)

| Calc. (×0.5 $H_2CO_3$): | C | 66.31 | H | 6.74 | N | 7.55 |
|---|---|---|---|---|---|---|
| Found | | 66.75 | | 6.85 | | 7.41 |

The following compounds are obtained analogously:

(1) 4-amidino-4'-[(4-methoxycarbonylmethyl-piperidino)-carbonyl]-biphenyl-hydrochloride
Melting point: 268°–270° C.

(2) 4-amidino-4'-[(4-methoxycarbonylmethyl-piperidino)-methyl]-biphenyl-hydrochloride
Melting point: 148°–150° C. (decomp.)

(3) 4-amidino-4'-[(4-methoxycarbonyl-cyclohexyl)-aminocarbonyl]-biphenyl-hydrochloride
Melting point: 302°–305° C. (decomp.)

(4) 4-amidino-4'-methoxy-3'-[(4-methoxycarbonyl-cyclohexyl)-aminocarbonyl]-biphenyl
$R_f$ value: 0.15 (silica gel; methylene chloride/methanol= 9:1)

(5) 4-amidino-4'-[N-(4-methoxycarbonyl-cyclohexyl)-N-methyl-aminocarbonyl]-biphenyl-hydrochloride
Melting point: 295°–300° C.

EXAMPLE L 1-(4'-amidino-4-biphenylyl)-3-methoxycarbonylmethyl-imidazolidin-2-one-hydrochloride To 3.1 g of 1-(4'-cyano-4-biphenylyl)-3-methoxycarbonylmethyl-imidazolidin-2-one are added 85 ml of a solution of hydrogen chloride in methanol, saturated whilst cooling with ice. The resulting suspension is covered with petroleum ether and stirred for 3.5 hours at ambient temperature. It is evaporated to dryness and dried a further 15 minutes at 1 mbar. The residue is suspended in 80 ml of absolute methanol, mixed with 2.7 g of ammonium carbonate and stirred for 16 hours at ambient temperature. The precipitate is filtered off, the mother liquor is evaporated under reduced pressure and the residue is purified by column chromatography on silica gel (eluant: methylene chloride/methanol/conc. ammonia=3:1:0.2).

Yield: 0.7 g (20% of theory),
Melting point: above 200° C.
$R_f$ value: 0.53 (silica gel; methylene chloride/methanol/conc. ammonia=3:1:0.2)

The following compounds are obtained analogously:
(1) 1-(4-amidino-phenyl)-3-[4-(2-methoxycarbonyl-ethyl) cyclohexyl]-imidazolidin-2-one-hydrochloride
Melting point: above 200° C.
$R_f$ value: 0.44 (Reversed Phase Plate RP8; methanol/5% sodium chloride solution=6:4)
(2) 1-(4-amidino-phenyl)-3-[4-(2-methoxycarbonyl-ethyl) phenyl]-imidazolidin-2,4-dione-hydrochloride
Melting point: above 260° C.
$R_f$ value: 0.19 (silica gel; methylene chloride/methanol= 9:1)

| Calc.: | C | 57.62 | H | 5.08 | N | 13.44 | Cl | 8.50 |
|---|---|---|---|---|---|---|---|---|
| Found: | | 56.94 | | 5.03 | | 13.33 | | 8.99 |

(3) 2-(4-amidino-phenyl)-5-[4-(2-methoxycarbonyl-ethyl) phenyl]-1,2,5-thiadiazolidin-1,1-dioxide-hydrochloride
Melting point: 245°–248° C. (decomp.)
$R_f$ value: 0.44 (Reversed Phase Plate RP8; methanol/10% sodium chloride solution=6:4)
(4) 1-(4-amidino-phenyl)-3-[4-(2-methoxycarbonyl-ethyl) phenyl]-4-methyl-imidazolin-2-one-hydrochloride
Melting point: 248° C. (decomp.)
$R_f$ value: 0.40 (Reversed Phase Plate RP8; methanol/5% sodium chloride solution=6:4)
(5) 2-(4-amidino-phenyl)-4-[4-(2-methoxycarbonyl-ethyl) phenyl]-5-methyl-1,2,4-triazol-5-in-3-one-hydrochloride
Melting point: 272°–274° C.
$R_f$ value: 0.37 (Reversed Phase Plate RP8; methanol/5% sodium chloride solution=6:4)
(6) 2-(4-amidino-phenyl)-5-ethyl-4-[4-(2-methoxycarbonylethyl)-phenyl]1,2,4-triazol-5-in-3-one-hydrochloride
Melting point: above 250° C.
$R_f$ value: 0.36 (Reversed Phase Plate RP8; methanol/10% sodium chloride solution=6:4)

| Calc. × HCl: | C | 58.67 | H | 5.63 | N | 16.29 | Cl | 8.25 |
|---|---|---|---|---|---|---|---|---|
| Found: | | 58.01 | | 5.65 | | 16.26 | | 9.14 |

(7) 2-(4-amidino-phenyl)-4-[4-(2-methoxycarbonyl-ethyl) phenyl]-1,2,4-triazol-5-in-3-one-hydrochloride
Melting point: 275°–277° C.
$R_f$ value: 0.55 (Reversed Phase Plate RP8; methanol/5% sodium chloride solution=6:4)
(8) 4-(4-amidino-phenyl)-2-[4-(2-methoxycarbonyl-ethyl) phenyl]-1,2,4-triazol-5-in-3-one-hydrochloride
Melting point: 289°–291° C. (decomp.)
$R_f$ value: 0.49 (Reversed Phase Plate RP8; methanol/5% sodium chloride solution=6:4)

EXAMPLE M 2-(4-Amidino-phenyl)-5-[(3-methoxycarbonyl-propyl) aminocarbonyl]-1-methyl-benzimidazole-hydrochloride 4.2 g of methyl 4-[4-[N-(4-amidino-benzoyl)-methylamino]-3-nitro-benzoylamino]-butyrate are dissolved in 100 ml of methanol, mixed with 10 ml of ethereal hydrochloric acid and 0.5 g of 10% palladium charcoal and treated at ambient temperature with hydrogen under 5 bars of pressure for 22 hours. A further 0.3 g of catalyst are added and the mixture is reacted for another hour. The catalyst is filtered off, the filtrate is evaporated under reduced pressure and the residue is stirred with a mixture of 100 ml of ethyl acetate and 10 ml of methanol at ambient temperature for one hour, whereupon the substance is obtained in crystalline form.

Yield: 3.7 g (100% of theory),
Melting point: above 200° C.
$R_f$ value: 0.65 (Reversed Phase Plate RP18; methanol/5% aqueous sodium chloride solution=6:4)

The following compound is obtained analogously:
(1) 2-(4-amidino-phenyl)-5-[(2-methoxycarbonyl-ethyl) aminocarbonyl]-1-methyl-benzimidazole
$R_f$ value: 0.59 (Reversed Phase Plate RP18; methanol/5% aqueous sodium chloride solution=6:4)

EXAMPLE N

2-[(4-Amidino-phenyl)-oxymethyl]-5(6)-methoxycarbonylmethoxybenzimidazole-hydrochloride 2.4 g of 2-[(4-cyano-phenyl)-oxymethyl]-5(6)-methoxycarbonylmethoxy-benzimidazole are suspended in 300 ml of methanol. Hydrogen chloride gas is piped into the mixture for one hour at 0°–10° C. and the mixture is stirred for 4 hours at 15°–20° C. The methanol is evaporated off in vacuo, the residue is combined with 75 ml of methanol and this is in turn distilled off in vacuo. The residue is suspended in 300 ml of methanol, after which 16.3 g of ammonium carbonate are added in batches with stirring and the resulting mixture is stirred for a further 16 hours. The reaction mixture is adjusted to pH 4 with a mixture of 3 parts of methanol and one part of concentrated hydrochloric acid. It is then evaporated to dryness and the residue is purified over silica gel (eluant: methylene chloride/methanol=3:1 to 0:1).

Yield: 0.9 g (32% of theory),
Melting point: 250° C. (decomp.)
$R_f$ value: 0.64 (silica gel; methylene chloride/methanol/glacial acetic acid=3:1:0.1)

| Calc: × H$_2$O × HCl: | C | 52.87 | H | 5.18 | N | 13.70 | Cl | 8.67 |
|---|---|---|---|---|---|---|---|---|
| Found: | | 53.07 | | 5.02 | | 13.81 | | 8.80 |

The following compounds are obtained analogously:
(1) 2-(4-amidino-phenyl)-1-[2-(3,4-dimethoxy-phenyl)-ethyl]-5-[(2-methoxycarbonyl-ethyl)-aminocarbonyl]-benzimidazolehydrochloride
$R_f$ value: 0.20 (silica gel; ethyl acetate/ethanol=7:3)
(2) 2-(4-amidino-phenyl)-5-[(2-methoxycarbonyl-ethyl)-amino-carbonyl]-1-(2-piperazino-ethyl)-benzimidazole
Melting point: 80° C. (decomp.)
$R_f$ value: 0.14 (silica gel; isopropanol/water/conc. ammonia=7:2:1, after developing twice)
(3) 2-(4-amidino-phenyl)-5-[(2-methoxycarbonyl-ethyl) aminocarbonyl]-1-(3-thiomorpholino-propyl)-benzimidazole $R_f$ value: 0.18 (silica gel; methylene chloride/methanol/conc. ammonia=8:2:0.1)

Preparation of the end products:

Example 1

(3S,5S)-5-[(4'-Amidino-4-biphenylyl)oxymethyl]-3-[(methoxycarbonyl)methyl]-2-pyrrolidinone-hydrochloride[3-3H-4-biphenylyl]

In a sealed apparatus, a solution of 25 mg of (3S,5S)-5-[(4'-amidino-3-bromo-4-biphenylyl)oxymethyl]-3-[(methoxycarbonyl)methyl]-2-pyrrolidinone-hydrochloride in 0.5 ml of dimethylformamide is treated with 370 GBq of carrier-free tritium gas in the presence of 10 mg of a catalyst consisting of 10% palladium on activated charcoal, with vigorous stirring. After 4 hours the uptake of tritium has ceased. The reaction solution is diluted with some more dimethylformamide, the catalyst is filtered off and the solvent is removed under reduced pressure at 80° C. During this step, the majority of the labile tritium is removed. In order to remove the remaining labile tritium the residue is taken up in 50 ml of absolute ethanol, left to stand for 3 days at ambient temperature and then all the ethanol is removed at 35° C under reduced pressure. For storage the residue is taken up in 50 ml of absolute ethanol.

Radiochemical yield: 13.14 GBq (3.6% of theory, based on the total tritium activity used)

Radiochemical purity: 98.8% of theory

Method of determination HPLC:

| Column | 4 × 125 mm Kromasil 100, C 18, 5 μm |
|---|---|
| Flow | 1.5 ml/minute |
| Eluant A | 0.1% KH$_2$PO$_4$, pH 2.5 (H$_3$PO$_4$) |
| Eluant B | Methanol |
| Gradient | in 10 minutes from 95% A to 65% A, a further 20 minutes at 65% A |

Example 2

(3S,5S)-5-[(4,-Amidino-4-biphenylyl)oxymethyl]-3-[(carboxyl)methyl]-2-pyrrolidinone[$^3$-3H-4-biphenylyl]

A solution of 2.57 mg (1.577 GBq) of (3S,5S)-5-[(4'-amidino-4-biphenylyl)oxymethyl]-3-[(methoxycarbonyl)-methyl]-2-pyrrolidinone-[3-$^3$H-4-biphenylyl] in 6 ml of ethanol is evaporated down under reduced pressure at 35° C. The residue is dissolved in 300 μl of methanol and 50 μl of 2N sodium hydroxide solution are added (pH 12). After 12 hours at ambient temperature, first 600 μl of water are added and then ammonium chloride is added to give a pH of 8. Subsequently, a further 180 μl of water and 60 μl of methanol are added and this clear solution is chromatographed for purification on RP-8 ready-made thin layer plates (made by Merck; eluant: 60% methanol/40% 10% saline solution). The bands containing the title compound, which show up well under UV light (254 and 366 nm), are scratched away from the still damp plates, taking the usual precautions, and stirred thoroughly with 4 ml of dimethylsulphoxide and 200 μl of 1N hydrochloric acid. The suspension is filtered through a membrane filter, pore size 0.5 μm. 3.5 ml of solution of the [$^3$H] title compound are obtained.

Radiochemical purity: 97.8% of theory

Method of determination HPLC:

| Column | 4 × 125 mm Kromasil 100, C 18, 5 μm |
|---|---|
| Flow | 1.5 ml/minute |
| Eluant A | 0.1% KH$_2$PO$_4$, pH 2.5 (H$_3$PO$_4$) |
| Eluant B | Methanol |
| Gradient | in 10 minutes from 95% A to 65% A, a further 20 minutes at 65% A |

Identity: Shown by HPLC by comparison with inactive, analytically pure material.

Measurement of content (by UV spectrophotometry): 0.371 mg/ml

Activity concentration (liquid scintillation method): 258.5 MBq/ml

Specific activity: 256 GBq/mMol=0.697 MBq/mg

Chemical yield: 1.298 mg (57% of theory)

Example 3

(3S,5S)-5-[(4'-Amidino-4-biphenylyl)oxymethyl]-3-[(carboxy)-methyl]-2-pyrrolidinone[$^3$-H-4-biphenylyl]

A solution of 2.14 mg of (3S,5S)-5-[(4'-amidino-4-biphenylyl)oxymethyl]-3-[(methoxycarbonyl)methyl]-2-pyrrolidinone-hydrochloride[3-$^3$H-4-biphenylyl] in 5 ml of ethanol with a total radioactivity of 1.314 GBq is evaporated down at reduced pressure at 35° C. The residue is dissolved in 350 μl of methanol and 25 μl of 2N sodium hydroxide solution are added (pH 12). After 12 hours at ambient temperature the crystals precipitated are centrifuged onto the bottom of the reaction vessel and the clear supernatant is pipetted off. The crystalline residue is washed 3 times, each time with 100 μl of methanol, dissolved in 300 μl of dimethylsulphoxide and 40 μl of 1N hydrochloric acid and then adjusted to a total volume of 3 ml with additional dimethylsulphoxide.

Radiochemical yield: 425 MBq (32% of theory)

Chemical yield: 0.61 mg (32% of theory)

Identity: Demonstrated by HPLC by comparison with inactive, analytically pure material.

What is claimed is:

1. A method of testing binding capability of a chemical substance to fibrinogen receptors which comprises combining a chemical substance to be tested with an amidine of formula $$R_a\text{—}R_b, \qquad (I)$$

wherein $R_a$ represents a 4-amidinophenyl group, and $R_b$ represents an HOOC—D—C—B—A— group, wherein A represents an optionally methoxy-substituted phenylene group, B represents a methyleneoxy group bound to the group A via the oxygen atom, C represents a pyrrolidin-di-yl or pyrrolidinon-di-yl group substituted by the group $R_3$ at the nitrogen atom, and D represents a bond or a methylene or ethylene group, whilst $R_3$ represents a hydrogen atom, a 3-phenylpropyl, acetyl, methanesulphonyl or pyrrolidinocarbonylmethyl group, and at least one hydrogen atom in the amidine of formula (I) is replaced by tritium, or the salts thereof, and measuring the amount of chemical substance bound to the fibrinogen receptor.

2. An amidine of formula $$R_a\text{—}R_b, \quad (I)$$

wherein $R_a$ represents a 4-amidinophenyl group, and $R_b$ represents an HOOC—D—C—B—A— group, wherein A represents an optionally methoxy-substituted phenylene group, B represents a methyleneoxy group bound to the group A via the oxygen atom, C represents a pyrrolidin-di-yl or pyrrolidinon-di-yl group substituted by the group $R_3$ at the nitrogen atom, and D represents a bond or a methylene or ethylene group, whilst $R_3$ represents a hydrogen atom, a 3-phenylpropyl, acetyl, methanesulphonyl or pyrrolidinocarbonylmethyl group, and at least one hydrogen atom in the amidine of formula (I) is replaced by tritium, or the salts thereof.

3. The fibrinogen receptor antagonist as recited in claim 2, wherein $R_a$ represents a 4-amidino-phenyl group, $R_b$ represents a phenyl group which is substituted in the 4-position by a 4-carboxymethyl-pyrrolidin-2-yl-methyloxy or 3-carboxymethyl-pyrrolidin-2-on-5-yl-methyloxy group, whilst in the 1-position each pyrrolidine moiety may be substituted by an acetyl or methanesulphonyl group and the pyrrolidinone moiety may be substituted by a 3-phenyl-propyl or pyrrolidinocarbonylmethyl group, and the salts thereof.

4. The fibrinogen receptor antagonist as recited in claim 2, further characterized in that an aromatic hydrogen atom is replaced by tritium.

5. The fibrinogen receptor antagonist as recited in claim 2, (3S,5S)- and (3R, 5R)-1-acetyl-5-[(4'-amidino-4-biphenylyl)-oxymethyl]-3 -carboxymethylpyrrolidine, and the salts thereof.

6. The fibrinogen receptor antagonist as recited in claim 2, (3S,5S)-and (3R, 5R)-5 -[(4'-amidino-4-biphenylyl)-oxymethyl]- 3-carboxymethyl-1-methanesulphonyl-pyrrolidine, and the salts thereof.

7. The fibrinogen receptor antagonist as recited in claim 2, (3S,5S)-and (3R,5R)-5-[(4'-amidino-4-biphenylyl)-oxymethyl]-3-carboxymethyl-pyrrolidin-2-one, and the salts thereof.

8. The fibrinogen receptor antagonist as recited in claim 2, (3S,5S)-5-[(4'-amidino-4-biphenylyl)-oxymethyl]-3-carboxymethyl-pyrrolidin-2 -one[3-$^3$H-4-biphenylyl], and the salts thereof.

9. A method for determining concentration of fibrinogen antagonists in a mixture of various chemical substances which comprises mixing a tritium labeled amidine of formula $$R_a\text{—}R_b, \quad (I)$$

wherein $R_a$ represents a 4-amidinophenyl group, and $R_b$ represents an HOOC—D—C—B—A— group, wherein A represents an optionally methoxy-substituted phenylene group, B represents a methyleneoxy group bound to the group A via the oxygen atom, C represents a pyrrolidin-di-yl or pyrrolidinon-di-yl group substituted by the group $R_3$ at the nitrogen atom, and D represents a bond or a methylene or ethylene group, whilst $R_3$ represents a hydrogen atom, a 3-phenylpropyl, acetyl, methanesulphonyl or pyrrolidinocarbonylmethyl group, and at least one hydrogen atom in the amidine of formula (I) is replaced by tritium, or the salts thereof and measuring the amount of said amidine bound in the mixture.

10. The method of claim 9 wherein the mixture comprises albumin or other body fluids.

* * * * *

UNITED STATES PATENT AND TRADEMARK OFFICE
CERTIFICATE OF CORRECTION

PATENT NO. : 5,677,466

DATED : Oct. 14, 1997

INVENTOR(S) : J. Weisenberger et al.

It is certified that error appears in the above-identified patent and that said Letters Patent is hereby corrected as shown below:

On the title page, item [21],
The application number is 447,667, and not 477,667.

Signed and Sealed this

Third Day of February, 1998

*Attest:*

BRUCE LEHMAN

*Attesting Officer*   *Commissioner of Patents and Trademarks*